US00PP31281P2

(12) United States Plant Patent
Hansen

(10) Patent No.: US PP31,281 P2
(45) Date of Patent: Dec. 24, 2019

(54) ***HEUCHERA* PLANT NAMED 'SPEARMINT'**

(50) Latin Name: ***Heuchera* hybrid**
Varietal Denomination: Spearmint

(71) Applicant: Hans A Hansen, Zeeland, MI (US)

(72) Inventor: Hans A Hansen, Zeeland, MI (US)

(73) Assignee: Walters Garden Inc, Zeeland, MI (US)

( * ) Notice: Subject to any disclaimer, the term of this patent is extended or adjusted under 35 U.S.C. 154(b) by 0 days.

(21) Appl. No.: 16/350,494

(22) Filed: Nov. 21, 2018

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./263.1, 440
See application file for complete search history.

*Primary Examiner* — Susan McCormick Ewoldt
*Assistant Examiner* — Karen M Redden

(57) ABSTRACT

The new and distinct hybrid of *Heuchera* plant named 'Spearmint' with medium mostly flat foliage with rounded apices and shallowly dissected lobes. The leaf blades are without purplish undertones on top or below and develop a heavy silver overlay covering all but the dark green veins. Branched panicles are deep burgundy displaying two-tone dark pink and light pink calyces with light pinkish petals for about five weeks beginning mid-summer. The new plant is vigorous and produces large clumps with many large leaves.

1 Drawing Sheet

Botanical denomination: *Heuchera* hybrid.
Variety denomination: 'Spearmint'.

STATEMENT REGARDING PRIOR DISCLOSURES UNDER 37CFR 1.77(b)(6)

The first public disclosure of the claimed plant, in the form of a sale, was made by Walters Gardens, Inc. on Jul. 9, 2018. Prior to that, on Dec. 1, 2017 the claimed plant was displayed with a photograph and brief description in a website operated by Walters Gardens, Inc., who obtained the plant and all information relating thereto, from the inventor. No plants of *Heuchera* 'Spearmint' have been sold to the public, in this country or anywhere in the world, nor has any disclosure of the new plant been made, more than one year prior the filing date of this application, and such sale or public disclosure within one year was either derived directly or indirectly from the inventor.

BACKGROUND OF THE INVENTION

The present invention relates to a new and distinct cultivar of Coral Bells in the *Saxifragaceae* family and given the cultivar name of 'Spearmint'. *Heuchera* 'Spearmint' was hybridized by the inventor on Apr. 11, 2013 at a wholesale perennial nursery in Zeeland, Mich., USA. The seed or female parent was the proprietary, unreleased, unnamed hybrid known only by the breeder code 12-287-01 (not patented) and the pollen or male parent was 'Coral Forest' (not patented).

*Heuchera* 'Spearmint' was first selected in the fall of 2015 and passed final evaluation in the fall of 2016 from among many other seedlings from the same cross and hundreds of other crosses and assigned the breeder code 13-814-1 through the remaining evaluation process. *Heuchera* 'Spearmint' has been asexually propagated by division at the same nursery in Zeeland, Mich. in 2016 and by sterile, shoot-tip, tissue culture propagation, and the resultant plants have remained stable and continued to exhibit the same characteristics as the original plant for multiple generations.

BRIEF SUMMARY OF THE INVENTION

The nearest comparison varieties include: the male parent 'Coral Forest', 'Ruby Bells' (not patented), 'Appletini' U.S. Plant Pat. No. 29,396, 'Paris' U.S. Plant Pat. No. 18,881 and 'Stainless Steel' U.S. Plant Pat. No. 23,349. The male parent, 'Coral Forest' has similar reddish flowers, but the foliage has much less silver marbling. Neither the female parent nor photographs of the female parent exist, so no further comparison between 12-287-01 and the new plant are possible. 'Ruby Bells' has similar reddish flowers and less silver marbling. 'Appletini' has lighter chartreuse foliage with less silver marbling and the flowers are deeper red. 'Paris has less silver overlay between the veins and the leaves more dissected and are not as round. 'Stainless Steel' has larger near-white flowers and the foliage has is slightly more intense silver marbling but has more greyed-purple undertones on the bottom of the leaf and showing through on the top. *Heuchera* 'Spearmint' differs from its parents as well as all other coral bells known to the applicant in the following combined traits:

1. Medium rounded foliage with apices rounded and minutely apiculate.
2. Dark green leaves have heavy silver overlay and contrasting dark green region surrounding the veins without purplish undertones on top or underneath.
3. Leaf blades are shallowly dissected with apices rounded and apiculate.
4. Flower effect is dark pink distally and light pink proximally for five weeks in mid-summer.
5. The new plant is vigorous and produces medium dense clumps and many individual leaves.

BRIEF DESCRIPTION OF THE DRAWINGS

The photographs of the new plant demonstrate the overall appearance of the plant including the unique traits of a container-grown plant in a greenhouse in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
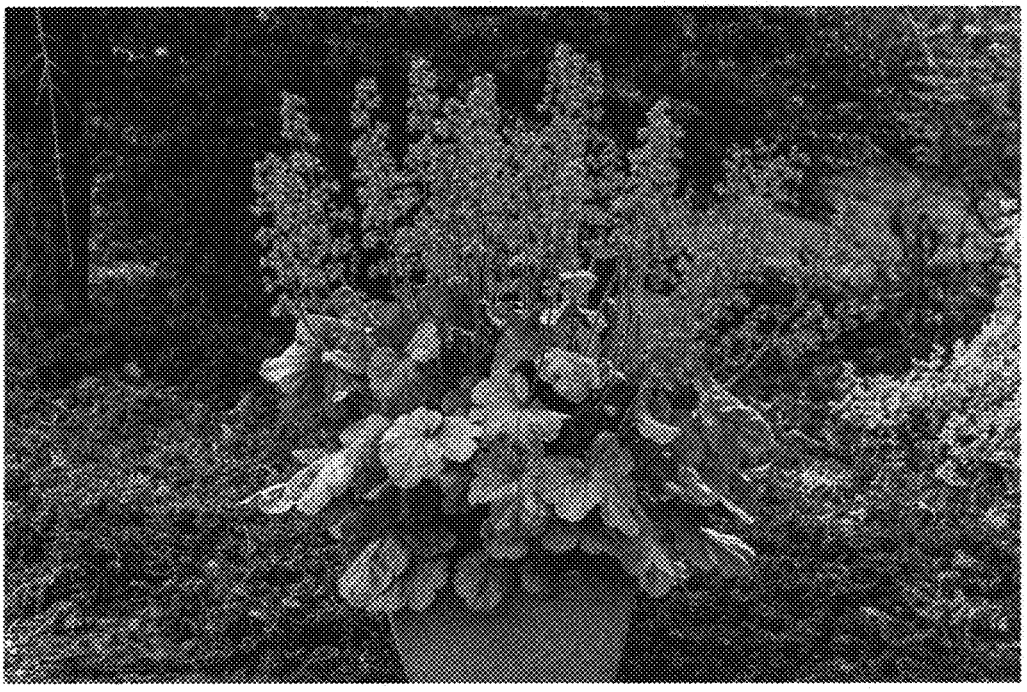
FIG. 1 shows a two-year-old plant with peak flowering.
Figure 2:
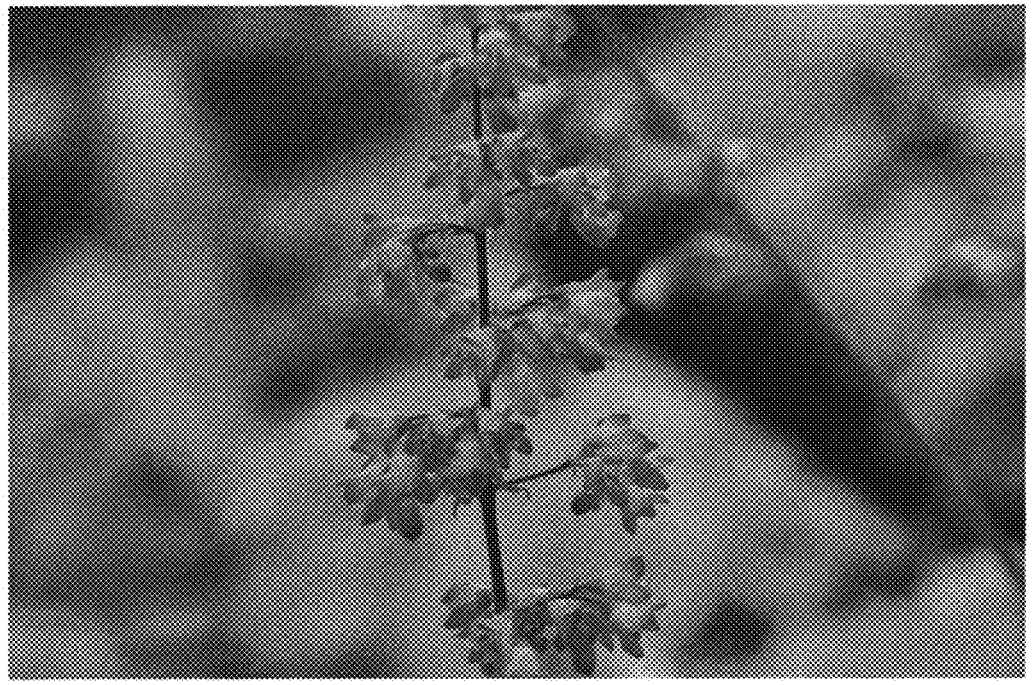
FIG. 2 shows a close-up of a flower panicle with buds and flowers from a two-year-old plant.

The following description is based on a two-year-old plant growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was the proprietary, unreleased hybrid known as 12-287-01 comprising crosses with 'Miracle' U.S. Plant Pat. No. 20,274, 'Ruby Bells' (not patented), 'Mocha' U.S. Plant Pat. No. 18,386 and 'Stainless Steel' U.S. Plant Pat. No. 23,349; the male or pollen parent was 'Coral Forest';

Plant habit: Hardy herbaceous perennial with basal rosette of foliage; mounded foliage about 26.0 cm tall and 58.0 cm in diameter with scapes to about 70.0 cm long; with 15 stems per plant to about 5.0 cm long and 1.5 cm diameter at base, about 16 to 20 leaves per stem;

Roots: Fibrous, finely branched;

Growth rate: Rapid, rooting from cutting in two weeks and finishing in three-liter container in about two and a half months;

Foliage: Rounded; apex and lobe apices rounded and minutely apiculate; base cordate with basal lobes frequently overlapping to about 1.0 cm; margins crenate, ciliolate, mucronulate; micro-puberulent adaxial and pubescent abaxial; palmately shallowly lobed with five main lobes dissected less than one-fifth of the way to petiole; lustrous adaxial and matte abaxial; held nearly horizontal; margin nearly flat, not sinuate;

Leaf blade size: To about 11.2 cm wide and 11.5 cm long, average about 9.8 cm wide and 9.5 cm long;

Leaf color: Spring and young emerging leaves adaxial between RHS 144A and RHS N144D with no silver and dark green marbling surrounding the veins, spring and young emerging leaves abaxial nearest RHS 145A; mature mid-season leaves adaxial nearest blend of RHS 189B and RHS 191A with dark green nearest RHS 136A surrounding the veins and blushed around the margin, abaxial mature mid-season leaves nearest RHS N138C; mid-fall color adaxial variable, nearest RHS 137A surrounding major veins, mixtures of blend of RHS 139D and RHS 194B distally and nearest RHS 194C; mid-fall abaxial blend nearest RHS 194C;

Leaf quantity: Dense, about 200 per plant;

Veins: Palmate, hirsutulous abaxial and glabrous adaxial; costate abaxial, slightly impressed to nearly flat adaxial;

Vein color: Emerging or early spring adaxial nearest RHS 145C with emerging spring abaxial nearest RHS 145D; mid-season and flowering time adaxial nearest RHS 145B in basal region near petiole and distally becoming nearest RHS 136A, mid-season and flowering time abaxial main veins nearest RHS 145C and secondary veins nearest RHS 137A; fall adaxial main veins nearest blend of RHS 146D and RHS 145A, fall abaxial main veins nearest 160D with distal and secondary veins becoming nearest RHS 138A;

Petiole: Cylindrical; base amplexicaul; with sparse pubescent hairs to about 2.0 mm long; to about 13.5 cm long and 4.0 mm wide above base stipules, average about 12.0 cm long and about 3.5 mm diameter above stipule;

Petiole color: Emerging leaf nearest RHS 145A; flowering season mature leaf nearest RHS 145C proximally and distally nearest RHS 146D;

Stipule: Flared at base of petiole; glaucous and glabrous abaxial and adaxial; margin ciliate; to about 14.0 mm long and about 12.0 mm wide at base; with two lateral projections of about 8.0 mm long in distal portion;

Stipule color: Young expanding leaf adaxial and abaxial nearest RHS 145C; mature leaf adaxial and abaxial nearest RHS 145D;

Peduncle: Panicle; cylindrical; stiff; pubescent; upright; with short branches; to about 70.0 cm long and 4.5 mm diameter at base, average about 64.0 cm tall and 4.0 mm diameter; about 40 per plant with up to about 165 flowers per panicle, average about 145; tightly-branched panicle with up to 16 branches up to 8.0 cm long and 1.0 mm diameter decreasing distally, average 14 branches per panicle; lower branches mostly upright becoming drooping distally; with about three cauline leaves about 3.5 cm apart before flowers and subtending branches; flower density heavy;

Cauline leaves: Palmate; incised margins to shallowly lobed; rounded with mucronate apex and lobes and truncate base; to 3.0 cm long and 3.3 cm across, decreasing distally; petiolate; petiole to 1.5 cm long and 2.0 mm across;

Cauline leaf color: Same as basal leaves;

Flowering longevity: Panicle effective for about four to five weeks; individual flowers about 5 days; self-cleaning;

Peduncle color: Nearest RHS 138A proximally and in regions without high light exposure and nearest RHS N187A with undertones of nearest RHS NN137B distally and in regions of high light exposure;

Pedicel: Cylindrical, pubescent; about 3.0 mm long and 0.5 mm diameter; attitude outwardly to drooping;

Pedicel color: Nearest RHS 187B;

Buds one day prior to opening: Ellipsoidal; rounded apex and attenuate base; puberulent to glandular; about 5.0 mm long and 3.5 mm diameter;

Bud color one day prior to opening: Distally nearest RHS 53A and proximally nearest RHS 53D;

Flower: Perfect; campanulate; actinomorphic; about 8.5 mm long to tip of exserted style and 5.5 mm in diameter at corolla face;

Flower attitude: Outwardly to drooping;

Calyx: Five, apex rounded, base fused in proximal 4.5 mm to form hypanthium; puberulent to glandular abaxial, glabrous adaxial; about 8.0 mm long and 5.0 mm wide at apex;

Sepals: Five; lanceolate; acute apex, fused in basal 4.5 mm; to about 8.0 mm long and 2.5 mm wide at fusion;

Sepal color: Abaxial nearest RHS 53B distally and nearest RHS 53D center and toward base with the base nearest RHS 174B, adaxial apex nearest RHS 53B becoming nearest RHS 53D toward base;

Petals: Five; oblanceolate to spatulate; subacute apex and attenuate base; entire; glabrous abaxial; micro-puberulent adaxial base; about 3.3 mm long and 1.2 mm wide in middle;

Petal color: Abaxial and adaxial nearest RHS 69B;

Androecium: Five adnate to adaxial sepal about 1.0 mm above base;

*Filaments.*—Five, thin, glabrous; about 2.5 mm long and less than 0.3 mm diameter; color nearest RHS 155B.

*Anthers.*—Ellipsoidal, distinct, basifixed, longitudinal; about 0.7 mm long and about 0.5 mm across; color nearest RHS 170B.

*Pollen.*—Abundant; color nearest RHS 17B.

Gynoecium: One, two-beaked; half-inferior; bifid style with pistil split at ovary; about 7.5 mm long;

*Style.*—Bifid; split apart at apex of ovary; exserted; about 5.5 mm long and about 0.5 mm diameter; color nearest RHS 75B.

*Stigma.*—Acute apex, about 0.1 mm diameter; color nearest RHS 75A.

*Ovary.*—Half-inferior, about 2.0 mm long and 2.0 mm diameter; ellipsoidal to globose, base rounded; color nearest RHS 162D.

Fruit: Small two-beaked capsule; about 2.5 mm long and 2.5 mm across; drying to RHS 200C;

Seeds: Abundant; slightly flattened ellipsoid; about 0.3 mm long, 0.2 mm across and about 0.1 mm thick; color nearest RHS 200A;

Disease and pest tolerance: The new plant grows best with ample moisture and drainage in either part sun or full shade. Cold hardy from USDA zones 4 to 9. Other resistance and tolerance outside of that normal for *Heuchera* is not known.

It is claimed:

1. The new and distinct coral bells plant named *Heuchera* 'Spearmint' as herein described and illustrated.

* * * * *